United States Patent [19]

McLean

[11] Patent Number: 4,893,424
[45] Date of Patent: Jan. 16, 1990

[54] METHOD AND APPARATUS FOR IDENTIFICATION OF HISTOLOGY SAMPLES

[76] Inventor: William McLean, 1 Hill Cottage, Bockelton, Tenbury Wells, England, WR15 8PP

[21] Appl. No.: 119,310

[22] Filed: Nov. 9, 1987

Related U.S. Application Data

[63] Continuation of Ser. No. 832,711, Feb. 14, 1986, abandoned.

[30] Foreign Application Priority Data

Jun. 17, 1984 [GB] United Kingdom ............... 8415648
Jun. 29, 1984 [GB] United Kingdom ............... 8416688

[51] Int. Cl.⁴ .............................................. G09F 23/00
[52] U.S. Cl. ..................................... 40/616; 40/635; 40/637; 264/158
[58] Field of Search .............. 40/2 C, 2 F, 629, 625, 40/635, 637, 628, 616; 264/158, 247; 434/296

[56] References Cited

U.S. PATENT DOCUMENTS

| | | | |
|---|---|---|---|
| 56,068 | 7/1866 | Lincoln | 40/2 C |
| 710,939 | 10/1902 | Berry | 40/2 C |
| 1,859,467 | 5/1932 | Rath | 40/2 F |
| 2,423,435 | 7/1947 | Block . | |
| 2,800,731 | 7/1957 | Carson | 40/629 |
| 3,052,999 | 9/1962 | Sedgwick et al. | 40/625 |
| 3,629,044 | 12/1971 | Sanger | 40/629 |
| 3,643,358 | 2/1972 | Morderosian | 40/629 |
| 4,096,655 | 6/1978 | Ullman, Jr. | 40/299 |
| 4,276,253 | 6/1981 | Adler, Sr. et al. | 264/158 |
| 4,640,035 | 2/1987 | Kind et al. | 40/326 |

FOREIGN PATENT DOCUMENTS 046940A 11/1980 United Kingdom .

*Primary Examiner*—Gene Mancene
*Assistant Examiner*—Cary E. Stone
*Attorney, Agent, or Firm*—Mattern, Ware, Stoltz & Fressola

[57] ABSTRACT

An identification marker (17) is described for use in permanently identifying an individual histology sample (21), the marker including columnar indicia (18) mounted on a base (19) having a location flange (20). A specially adapted cassette having a slot (16) to receive the identification marker is described together with apparatus and method for moulding the indicia in a protein such as agar agar. The use of the identification marker is described firstly mounted in the cassette (11) during treatment of the sample (21) and later mounted beneath the cassette (11) in the slot (16) for wax embedding of the sample and identification marker. The marker (17) is sectioned simultaneously with the tissue sample (21) by means of a microtome (31), each section taken being identified by a section through the identification marker embedded alongside the sample.

9 Claims, 4 Drawing Sheets

METHOD AND APPARATUS FOR IDENTIFICATION OF HISTOLOGY SAMPLES

This is a continuation of co-pending application Ser. No. 832,711 filed on Feb. 14, 1986, now abandoned.

BACKGROUND OF THE INVENTION

1. Technical Field

This invention relates to a method and apparatus for identification of histology samples. Many samples of tissue are taken for microscopic examination in the diagnosis and monitoring of a variety of illnesses and conditions. Before a microscopic examination can take place, a tissue sample must be treated to remove water, impregnated with an embedding medium such as wax, and then finally sectioned using a microtome. Suitable sections are then mounted on slides for examination.

Hospital and commercial laboratories have highly efficient systems for performing the necessary sequence of operations. Each tissue sample is placed in a perforated cassette which is marked with an identification number either manually in pencil or by hot foil stamping.

The cassette is closed with a lid and processed through the dehydration and wax impregnation stages. The sample is then emptied from the cassette into a stainless steel mould, the cassette is mounted on top of the mould and the whole assembly is set in wax. The stainless steel mould is removed, leaving the cassette with a wax block containing the treated sample moulded to its under-side. The identification number is still visible on the cassette to identify the sample.

The wax block and sample are then sliced using a microtome to provide sections for mounting on one or more slides. The cassette and the remainder of the sample are stored for future reference.

2. Background Art

At this stage it becomes necessary to transfer the identification number to each of the slides, either manually by pencilling onto a matt area on the slide or by manually scribing the slide with a diamond scriber or by the application of a computer printed label identical with that on the cassette. Great care is taken to ensure the correct labelling of all the slides but mistakes can occur.

It has also been proposed to prepare a cassette with the identification number etched by laser and to prepare some correspondingly identified slides. This requires considerable capital investment for the laser equipment and, particularly when it is not known how many slides will be needed for each sample, any surplus slides will be wasted because the number cannot be removed. With computer generated labels, any surplus labels must also be discarded but this is less expensive.

It has recently been proposed to form elongate labelling elements of a material which can be sectioned by microtome and to embed the labelling elements with the sample in the wax embedding medium. The elements are then sectioned with the tissue sample so that each slide will carry a thin section of the labelling elements to identify it.

However, the two stage relief moulding process proposed for making the elongate labelling elements would appear to be time consuming and incompatible with high speed laboratory processing. Further, the large size of the elements which would be formed by this process would require increased consumption of processing materials such as wax for even small tissue samples and larger cassettes.

DISCLOSURE OF THE INVENTION

From its broadest aspect, it is an object of the invention to provide a new or improved method and apparatus for permanently identifying an individual tissue sample sectioned for microscopic examination. Viewed from a further aspect, it is an object of the invention to provide a method and apparatus for identifying a tissue sample throughout the entire treatment cycle including sectioning for mounting on slides.

However, according to a specific aspect, the invention provides a new or improved form of identification marker for use in the permanent identification of an histology sample.

According to this aspect, there is provided an identification marker for use in permanent identification of an histology sample comprising a plurality of columnar indicia mounted on a base.

The indicia may be moulded integrally with the base and the base may have a location flange.

The identification marker may be made of a protein such as agar agar. An alternative material is gelatin.

The invention also provides a continuous strip of linked identification markers.

The invention provides apparatus for forming an identification marker comprising a plurality of hollow tubular indicia mould elements, disposed in an array; a base mould disposed beneath the indicia mould elements and primary casting means for introducing casting material into said indicia mould elements to form columnar indicia on said base mould.

The apparatus may include secondary casting means for casting material in the base mould before casting of said columnar indicia.

The array of tubular indicia mould elements may be provided on an array of adjacently disposed mould assemblies, each carrying a plurality of mould elements capable of being selectively positioned to produce an identification marker. For example, the mould elements may be provided on wheels having radial arms, each of which carries an indicia mould element, the wheels being adapted to be rotated to bring selected indicia mould elements into position to form said array.

According to the broadest aspect of the invention, there is provided a method of identifying an histology sample comprising placing the sample in a mould, placing an identification marker in the mould adjacent the sample, casting an embedding material such as wax in the mould to embed the sample and the identification marker in a single wax block, the identification marker being made of a material capable of being sectioned by microtome with the sample and comprising a plurality of columnar indicia mounted on a base, whereby microtome sections of the sample include a section of said indicia capable of identifying the individual histology sample.

According to a further aspect of the invention, there is provided a method of identifying histology samples comprising introducing an identification marker with the sample into an histology cassette; carrying out treatment processes on the cassette containing the sample and the identification marker; removing the sample to a mould for embedding in a medium such as wax; placing the identification marker in the mould adjacent the sample; casting wax in the mould to embed the sample and the identification marker in a single wax block; the identification marker being made of a material capable of passing through the treatment processes to be applied to the tissue sample including wax embedding and sectioning by microtome and comprising a plurality of columnar indicia mounted on a base whereby microtome sections of the sample include a section of said indicia capable of identifying the individual tissue sample.

The method may include attaching the identification marker to the cassette.

Preferably, the identification marker is attached inside the cassette while the sample is inside the cassette and the attachment of the identification marker is reversed so that it is attached to the underside of the cassette when the sample is removed to the mould for embedding, the cassette being placed on the mould and the wax being cast so as to mount the sample and the identification marker to the cassette.

Pre-treatment may be carried out on the identification marker before introduction into the cassette to make it resistant to the treatment processes to which the sample is to be subjected, for example to make the marker heat resistant. Where the identification marker is made of agar agar, this pre-treatment may comprise immersion for a period of approximately 10 minutes in an aqueous solution of formalin of a strength between 1 and 5% approximately.

The material for the identification marker may be stained either before or after moulding so that the indicia can be read easily when thinly sectioned on a slide. It may be stained in the course of treatment of the tissue sample.

The invention also provides a new or improved histology cassette for use in the identification of histology samples.

According to this aspect of the invention, an histology cassette is characterised in that it comprises a slot in which the identification marker may be mounted and against the border of which the flange locates. Preferably the identification marker may be mounted either within the cassette with the flange above the slot and the base disposed in the slot; or below the cassette with the flange above the slot and the indicia in the slot.

Cooperating location means for locating the identification marker inside the cassette may be provided on a lid of the cassette.

For example, a pair of ribs or a thin recessed portion of the lid material may be provided. Where the recessed portion is provided, the lid is preferably of a transparent or translucent material, whereby the indicia can be read through the lid while the sample is being processed inside the cassette.

BRIEF DESCRIPTION OF THE DRAWINGS

The invention will now be described in more detail by way of example only with reference to the accompanying drawings in which.

MODE OF CARRYING OUT THE INVENTION

Figure 1:
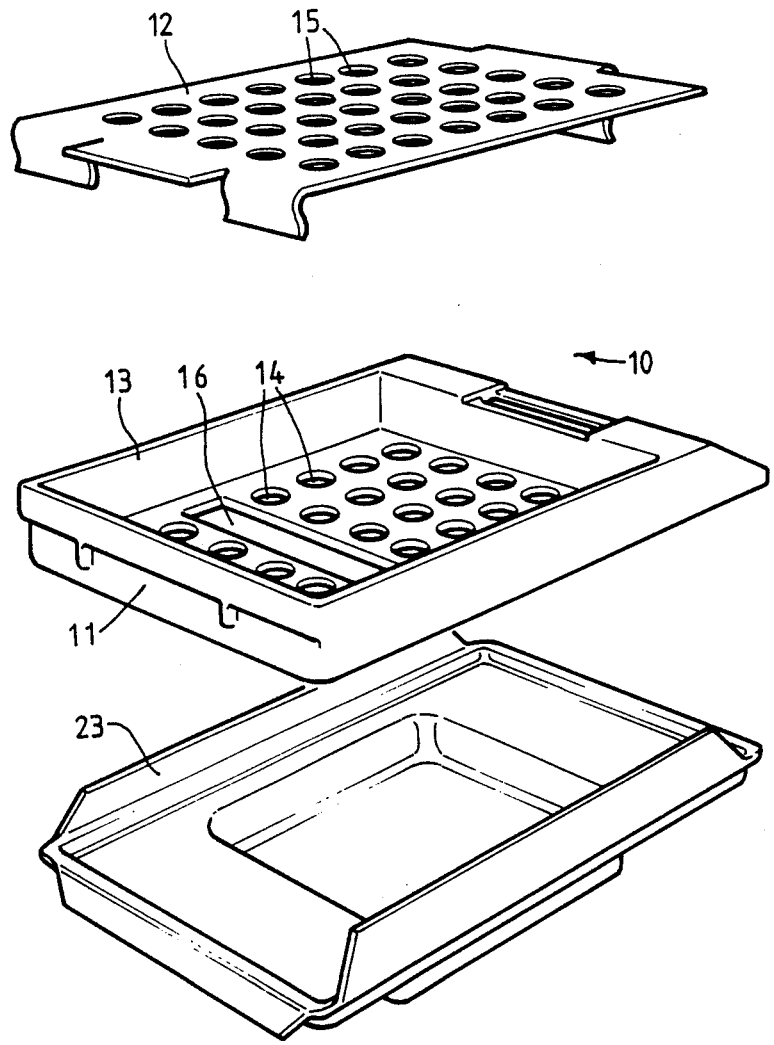
FIG. 1 is an exploded perspective view of an histology cassette.

Referring firstly to FIG. 1 of the drawings, a cassette assembly generally indicated at 10 comprises a cassette 11 and a lid 12. The cassette is in the form of a shallow box having walls 13 and a base 14 with perforations, through which treatment media can percolate during treatment of a sample for microscopic examination. The sample is placed into the cassette 11 and the lid 12 is attached by snap engagement with the cassette 11 or in some other manner. It is also possible to arrange the lid 12 as an integral hinged flap on the cassette 11.

The lid 12 also has holes 15 for treatment media to pass through.

Figure 7:
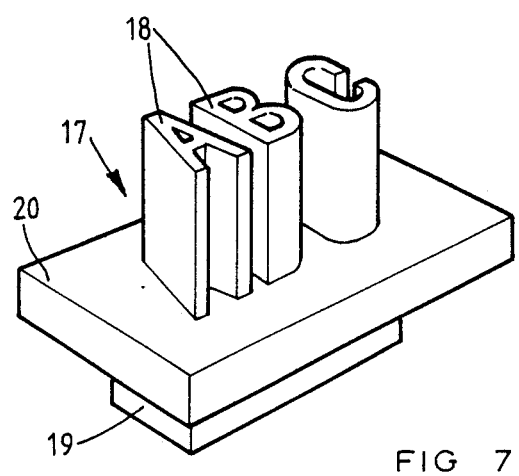
FIG. 7 is a perspective view of a typical identification marker, FIG. 8 diagrammatically illustrates an apparatus and method for moulding the identification marker.

In the base of the cassette, a slot 16 is provided to receive an identification marker indicated at 17 in the remaining figures of the drawings. A typical identification marker 17 is shown in FIG. 7 and comprises columnar indicia 18 arranged in an array on a base 19, with a surrounding peripheral flange 20 between the base and the indicia, the whole marker preferably being cast integrally in one piece.

Figure 2:
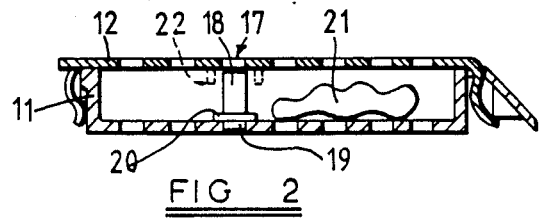
FIG. 2 is a vertical section of the cassette containing a sample and an identification marker in position for processing of the tissue sample.

For the initial processing of an histology sample 21, the identification marker 17 is positioned as shown in FIG. 2 of the drawings. It is placed with the indicia 18 inside the cassette 11, the flange 20 resting on the base of the cassette and the base 19 of the identification marker 17 projecting through the slot 16. The sample 21 is placed alongside the identification marker 17 and lid 12 is added to the cassette. The cassette is then passed through the various treatment stages which are necessary to prepare the sample 21 for microscopic examination. For example, the cassette is placed in baths of treatment media, at specific temperatures for specific periods. The objective is to remove the water from the tissue sample and thoroughly impregnate it with wax.

Throughout this treatment, the identification marker 17 remains associated with the sample so that the sample can be identified at any time. The identification marker can be visible through the lid 12 of the cassette if for example the lid is made of a fine gauze-like material or is made of a transparent plastic. The lid 12 may be provided with locating means such as ribs 22 to keep the identification marker 17 in an upright condition. Alternatively, a portion (not shown) of the lid 12 positioned opposite the slot 16 in the cassette may be thinner than the rest of the lid and may provide both a location and a reduced thickness "window" through which the identification marker can be seen.

The details of the identification marker itself will be referred to later but it is important that the material of which it is made has certain features.

Firstly, when the identification marker is to be treated with the sample, the material must not be such as to react adversely with a tissue sample 21 or with any of the process media used to treat the sample. The identification marker material must also be capable of passing through the treatment cycle without being damaged or destroyed. If necessary, the identification marker can be pre-treated before insertion in the cassette to make it more resistant to the processing which the sample has to undergo.

A preferred material for the identification marker is a protein derived from sea-weed known as agar agar. This material has a jelly-like consistency, is mouldable and is solid at room temperature. The identification marker can be pre-treated by soaking for approximately 10 minutes in an aqueous solution of formalin. The strength of the formalin solution may be for example between 1 and 5% by volume. The marker can be stained after moulding or made from pre-stained material.

Figure 6:
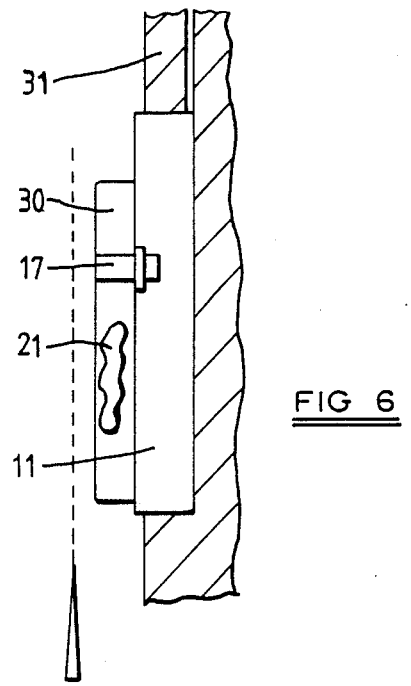
FIG. 6 shows the position of the sample and identification marker in the wax block during microtome slicing.

For the initial processing of the sample, up to the point where it is saturated in wax, all the treatments are carried out in the closed cassette. However, in order to slice the sample, it is necessary that it should be embedded in a wax block capable of being held in the chuck of a microtome as shown in FIG. 6 of the drawings.

Figure 3:
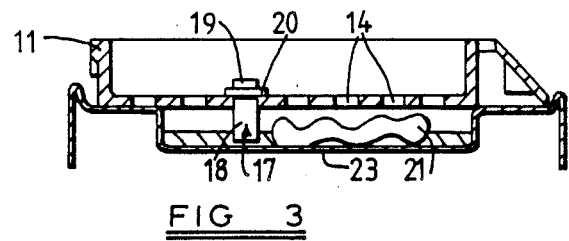
FIG. 3 is a similar section of the cassette, showing the sample and identification marker in position prior to wax embedment and the cassette located on a mould, containing a small amount of wax.

For wax embedding, the sample 21 is removed from the cassette and placed into a mould 23, conventionally of stainless steel. The mould may be re-usable. At this stage, the identification marker 17 is reversed in the base of the cassette so as to project downwardly as shown in FIG. 3 of the drawings. Thus, the indicia 18 project down into the mould 23 and are held in position by the location of the flange 20 on the base of the cassette around the slot 16.

In order to treat different sizes of sample, it is conventional to use differently sized base moulds in which a smaller or larger recess is provided to form the wax block around the sample. Where a small sized base mould is to be used, it is envisaged that the type of cassette used would have the slot 16 positioned more centrally than that shown in the drawings. Where a larger sample is to be embedded, the cassette shown in the drawings, together with a large sized base mould would be used.

The mould 23 is partly filled with wax 30 before the sample is added. More wax is then added and allowed to flood up into the base of the cassette 11 through the holes 14. Thus, the sample 21 and the identification marker 17 both become embedded in the wax 30, and the wax is keyed to the underside of the cassette 11, which in turn provides a firm location for inserting the sample in the chuck 31 of a microtome.

Figure 4:
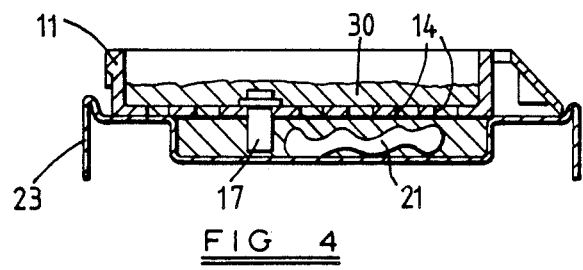
FIG. 4 shows the assembly of cassette and mould during wax embedment.
Figure 5:
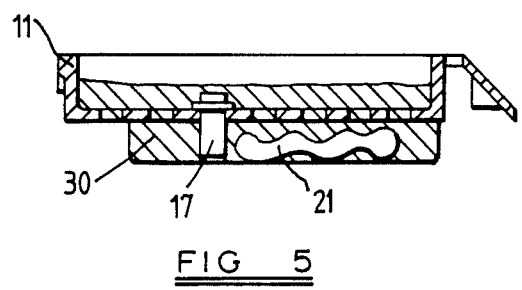
FIG. 5 shows the cassette, embedded sample and identification marker after removal of the mould.

FIG. 4 shows the wax embedding process with the wax flooding up through the cassette. FIG. 5 of the drawings shows the final wax block 30, now removed from the mould 23 and ready for slicing. It will be seen that the indicia 18 of the identification marker lie alongside the sample in the wax mould and, because of the columnar shape of these indicia, each slice taken of the sample will be accompanied by a section through the identification marker carrying the indicia. Thus, each sample will be permanently identified by having its identification marking clearly visible in the sectioned material. No further marking of the slides is necessary.

Similarly, the portion of the sample which has not been sliced but which is kept attached to the cassette for storage, possibly for future investigation, is permanently marked by the presence of the remainder of the identification marker 17.

Clearly, the material of which the marker is made must not only be capable of being finely moulded to produce legible indicia of relatively small size and be capable of withstanding the treatment processes applied to the tissue but must also be capable of being sliced in a microtome.

Since what is required is a material which behaves something like human tissue, it is believed that a protein jelly-like substance such as agar agar is particularly suitable.

Figure 8:
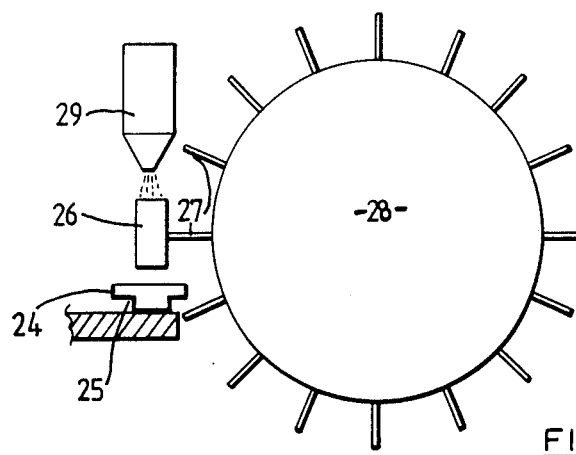
Figure 9:
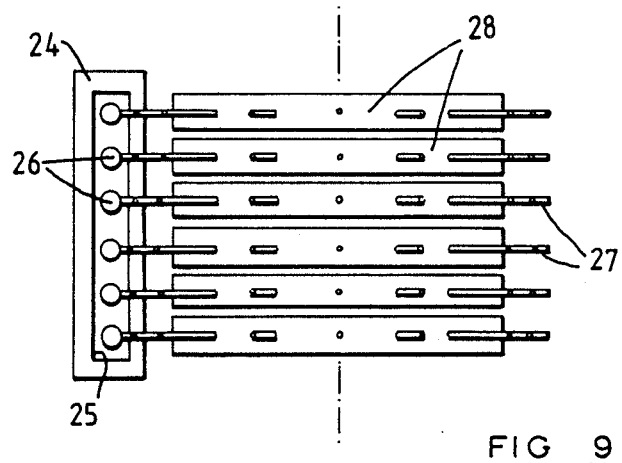
FIG. 9 is a diagrammatical plan view of the apparatus of FIG. 8.

FIGS. 8 and 9 illustrate diagrammatically one method by which an identification marker may be produced for use in the method described above Each identification marker 17 is moulded using a marker mould 24 having a step 25 in its base, to define the base 19 and flange 20 of the finished marker.

Each indicium is formed by an individual tubular mould element 26 which is carried on an arm 27 mounted on a wheel 28. The wheel 28 is rotatable about a central axis to bring the appropriate mould element 26 into a vertical position.

As will be seen from FIG. 9 of the drawings, a number of wheels 28 are mounted side by side on one or more axes and rotated to bring an array of mould elements 26 into line, each element being vertical.

The marker mould 24 is slid into position under the array of indicia mould elements 26 and the moulding material of which the identification marker is to be made is supplied to the individual indicia mould elements through spigots 29. All the moulding material can be supplied through the spigots 29, including that used for forming the base and flange.

Alternatively, a separate secondary moulding source may be provided to fill the marker mould 24 up to a certain level before it is introduced under the indicia mould elements 26.

As a further alternative, the indicia mould elements 26 may form risers which cooperate with the marker mould 24, the material being flooded up through the indicia mould elements on being filled into the marker mould 24.

The indicia mould elements are preferably heated to prevent premature solidification of the moulding material. When filling is complete, the material is allowed to solidify in the marker mould and in the indicia mould element, from which it is then ejected by for example a low pressure air jet. The mould elements and marker mould may be chilled to encourage setting of the material once mould filling has been completed.

For rapid preparation of identification markers, the moulding apparatus is preferably micro processor controlled so that a key board operator can pre-program the arrangement of the indicia mould elements to produce specific identification markers as required. In high speed laboratory work, where a technician may embed 50 to 100 samples per hour, a rapid and orderly production of identification markers is required. It is preferred that the markers should be produced in a continuous strip which can be achieved by linking the base moulds in to a continuous strip at the secondary moulding source before they are introduced to the primary moulding apparatus for the addition of the indicia.

Although the array of indicia mould elements can be controlled manually or by automatic indexing means, it is preferred that programmable micro processor control is used since this enables greater flexibility to be brought in to the system, producing if required several markers having the same indicia or producing indicia out of sequence.

In the foregoing description, it has been assumed that the indicia will be letters or numbers but they could of course be or include other symbols. It is also possible to devise a form of machine readable identification marker using for example simplified bar codes.

It has been assumed above that identification of the sample has been necessary during treatment processes in the cassette. If this is not a requirement, the identification marker can be introduced at the wax embedding stage, or merely placed in the cassette during treatment of the sample without location being necessary. In this case no slot need be provided and a conventional standard cassette can be used with a standard lid.

The material of the identification marker may be coloured by staining before or after moulding or during tissue processing or by the addition of a filler, for good visibility.

I claim:

1. An identification marker for use in permanent identification of a histology sample comprising a plurality of columnar indicia moulded integrally with a base, the indicia extending from the base in a protruding manner, the marker consisting solely of a single mouldable jelly-like material capable of being sliced by microtome and dimensionally sized for embedding within an embedding medium along with a histology sample.

2. A marker according to claim 1 wherein the base has a location flange.

3. A marker according to claim 1 wherein the jelly-like material is agar agar.

4. A marker according to claim 1 wherein the jelly-like material is gelatin.

5. A continuous strip of linked identification markers according to claim 1.

6. An identification marker for permanent identification of a histology sample in combination with an embedding medium and a histology sample, said identification marker comprising a plurality of columnar indicia moulded integrally with a base and extending from the base in a protruding manner, the marker consisting solely of a single mouldable jelly-like material capable of being sliced by microtome and being embedded with said embedding medium along with said histology sample.

7. A combination according to claim 6 wherein the base has a location flange.

8. A combination according to claim 6 wherein the jelly-like material is agar agar.

9. A combination according to claim 6 wherein the jelly-like material is gelatin.

* * * * *